(12) United States Patent
Abal

(10) Patent No.: US 10,300,219 B2
(45) Date of Patent: May 28, 2019

(54) AIR IN-LINE SENSING SYSTEM FOR IV INFUSION LINES

(71) Applicant: CareFusion 2200, Inc., San Diego, CA (US)

(72) Inventor: Daniel Abal, San Diego, CA (US)

(73) Assignee: CAREFUSION 2200, INC., San Diego, CA (US)

(*) Notice: Subject to any disclaimer, the term of this patent is extended or adjusted under 35 U.S.C. 154(b) by 34 days.

(21) Appl. No.: 14/721,928

(22) Filed: May 26, 2015

(65) Prior Publication Data
US 2016/0346484 A1    Dec. 1, 2016

(51) Int. Cl.
*A61M 5/36* (2006.01)
*A61M 5/168* (2006.01)

(52) U.S. Cl.
CPC .......... *A61M 5/36* (2013.01); *A61M 5/16831* (2013.01); *A61M 5/365* (2013.01); *A61M 2205/12* (2013.01)

(58) Field of Classification Search
CPC .... A61M 5/36; A61M 5/16831; A61M 5/365; A61M 2205/12
See application file for complete search history.

(56) References Cited

U.S. PATENT DOCUMENTS

| | | | |
|---|---|---|---|
| 4,303,376 A * | 12/1981 | Siekmann | A61M 5/14224 417/360 |
| 4,722,224 A | 2/1988 | Scheller et al. | |
| 4,829,448 A | 5/1989 | Balding et al. | |
| 4,842,584 A * | 6/1989 | Pastrone | A61M 5/14224 604/153 |
| 5,382,232 A | 1/1995 | Hague et al. | |
| 5,603,613 A * | 2/1997 | Butterfield | A61M 5/14228 417/474 |
| 6,489,896 B1 | 12/2002 | Platt et al. | |
| 6,616,633 B1 | 9/2003 | Butterfield et al. | |
| 2002/0159900 A1 | 10/2002 | Lawless et al. | |
| 2004/0115068 A1 | 6/2004 | Hansen et al. | |
| 2012/0181226 A1 | 7/2012 | Lauer | |

OTHER PUBLICATIONS

International Search Report and Written Opinion for Application No. PCT/US2016/012731, dated May 4, 2016, 16 pages.
Extended European Search Report for Application No. 16800405.9, dated Dec. 19, 2018, 7 pages.

* cited by examiner

*Primary Examiner* — Lauren P Farrar
(74) *Attorney, Agent, or Firm* — Morgan, Lewis & Bockius LLP

(57) ABSTRACT

A pump cassette body for detecting air bubbles in a fluid pathway, comprises an upstanding flow director vane, a fitment integrally molded into the pump cassette body, wherein the fitment comprises a base integrally molded into the pump cassette body, an elastomeric member attached to the base, and a housing at least partially surrounding the elastomeric member, wherein the elastomeric member is co-molded to the housing.

18 Claims, 15 Drawing Sheets

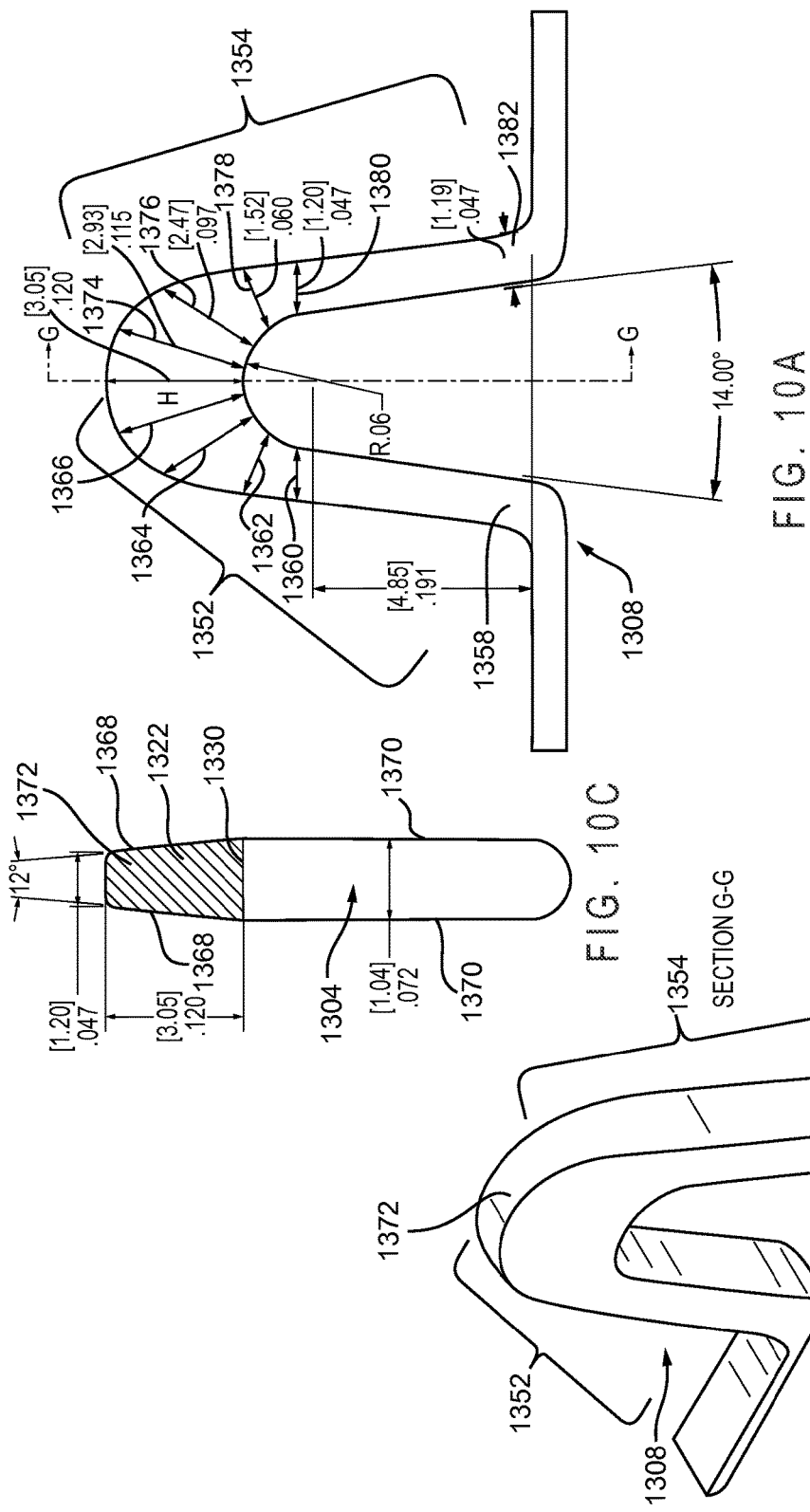

AIR IN-LINE SENSING SYSTEM FOR IV INFUSION LINES

TECHNICAL FIELD

The present disclosure generally relates to apparatus, systems, and methods of monitoring the delivery of medical fluid to patients, and more particularly to monitoring IV infusion lines and detecting gaseous air bubbles that may be present in IV infusion lines and associated methods.

BACKGROUND

Infusion pumps are medical devices that may be used to administer intravenous (IV) fluids. An infusion pump can facilitate the delivery of IV fluids while controlling the volumes and rates for the delivery of such IV fluids. The IV fluids may be delivered at continuous rates or intermittent intervals. Some infusion pumps move fluid through an IV tube using a peristaltic pumping mechanism that acts on the IV tube, while other infusion pumps rely on a cartridge or cassette-like device intended to be manipulated by a pump to cause the IV fluid to flow at the controlled rate or interval. In either case, a typical infusion pump, manipulates the IV tube or IV cartridge such that the IV fluid moves from a container to a patient. The IV tube or IV cartridge is typically connected to or integrated with an IV set (e.g., tubing, valves, and fittings for delivering fluid to a patient), and therefore the cartridge and IV set may be disposable to reduce the risk of infection and contamination.

Infusion pumps often include sensors that are used to detect gaseous air bubbles in the IV infusion fluid. Detection of such air bubbles is necessary in order to alarm a user or a clinician of a potential hazard that may cause an air embolism. In some sensing systems, the IV tube must be threaded into the pocket of the sensor to ensure the required coupling between the sensor and the IV tube is achieved. Misloading of the IV tube can occur when insufficient force is applied to insert the tubing into the sensor adequately, which can cause the tubing to move away from the sensing area and create false alarms. Furthermore, the tubing can creep over time as the force between the tubing and the sensor relaxes. This can result in an uncoupling of the sensor and the IV tube, which can also lead to false alarms. Another issue arises when air bubbles become stationary within the sensor gap due to non-optimization of the fluid flow path. This can lead to an acoustic short circuit. Additionally, IV tubing may be constructed of many different types of material. Since the sensor relies on acoustic measurements, it must be calibrated to the material used in the tubing. Moreover, because of manufacturing variations in the construction of the tubing, the material properties often vary which leads to additional non-optimization between the sensor and the tubing and again to false alarms. In other systems, such as a cassette, the air-in-line detection means is configured as a u-shaped structure that fits into an ultrasonic detector, such as shown in U.S. Pat. No. 4,842,584. These types of systems also suffer from certain deficiencies and while some improvements have been made to correct some of these deficiencies, such as those shown in U.S. Pat. No. 8,801,656, there still exists a need to further improve the sensing capacity and resistance to false alarms in these types of sensors.

SUMMARY

Aspects of the subject technology relate to a disposable pump cassette body for use in infusion systems. In accordance with certain aspects, a pump cassette body for detecting air bubbles in a fluid pathway, comprises an upstanding flow director vane, a fitment integrally molded into the pump cassette body, wherein the fitment comprises a base integrally molded into the pump cassette body, an elastomeric member attached to the base, and a housing at least partially surrounding the elastomeric member, wherein the elastomeric member is co-molded to the housing.

In accordance with another aspect, a pump cassette body for detecting air bubbles in a fluid pathway comprises a tapered U-shaped fluid flow path defined therein, the tapered fluid flow path having its largest volume at a top portion of the U-shape of the fluid flow path, with the volume tapering down moving away from the top portion of the U-shape of the fluid flow path, the fluid flow path passing through a fluid pathway extension member that is upstanding from the pump cassette body.

In accordance with another aspect, a system for detecting air bubbles in a fluid pathway comprises a pump cassette body having an upstanding flow director vane, a fitment integrally molded into the pump cassette body, wherein the fitment comprises a base integrally molded into the pump cassette body, an elastomeric member attached to the base, a housing at least partially surrounding the elastomeric member, wherein the elastomeric member is co-molded to the housing, a pump cassette recess having a slot defined therein, the slot substantially matching the dimensions of the fitment and having opposing walls, and an acoustic sensor disposed within the pump cassette recess, the acoustic sensor comprising a transmitter and a receiver, the transmitter and receiver being disposed behind opposite opposing walls of the slot.

In accordance with another aspect, a system for detecting air bubbles in a fluid pathway comprises a pump cassette body having an upstanding flow director vane, a fitment integrally molded into the pump cassette body, wherein the fitment comprises a base integrally molded into the pump cassette body, an elastomeric member attached to the base, a housing at least partially surrounding the elastomeric member, a pump cassette recess having a slot defined therein, the slot substantially matching the dimensions of the fitment and having opposing walls such that insertion of the fitment into the slot creates a compression load between the fitment and the walls of the slot, and an acoustic sensor disposed within the pump cassette recess, the acoustic sensor comprising a transmitter and a receiver, the transmitter and receiver being disposed behind opposite opposing walls of the slot.

In accordance with another aspect, a method of detecting air bubbles in a fluid pathway comprises the steps of providing a pump cassette having an upstanding fitment that includes a tapered fluid flow path therein, the tapered fluid flow path being formed between an upstanding flow director vane and an elastomeric member, the elastomeric member being co-molded to a housing, providing a pump cassette recess having an opening that substantially matches the upstanding fitment and includes a sensor having a transmitter and a receiver disposed on opposite sides of the opening, inserting the pump cassette into the pump cassette recess such that the fitment is inside the opening, sending an acoustic signal from the transmitter to the receiver across the fluid flow path, pumping a fluid through the fluid flow path, and detecting whether the acoustic signal is received by the receiver.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 10A illustrates a plan view of the flow channel of the embodiment of FIG. 10, in accordance with aspects of the present disclosure.

FIG. 10B illustrates a cross-sectional view of the flow channel of the embodiment of FIG. 10, in accordance with aspects of the present disclosure.

FIG. 10C illustrates a side view of the flow channel and flow director vane of the embodiment of FIG. 10, in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1A:
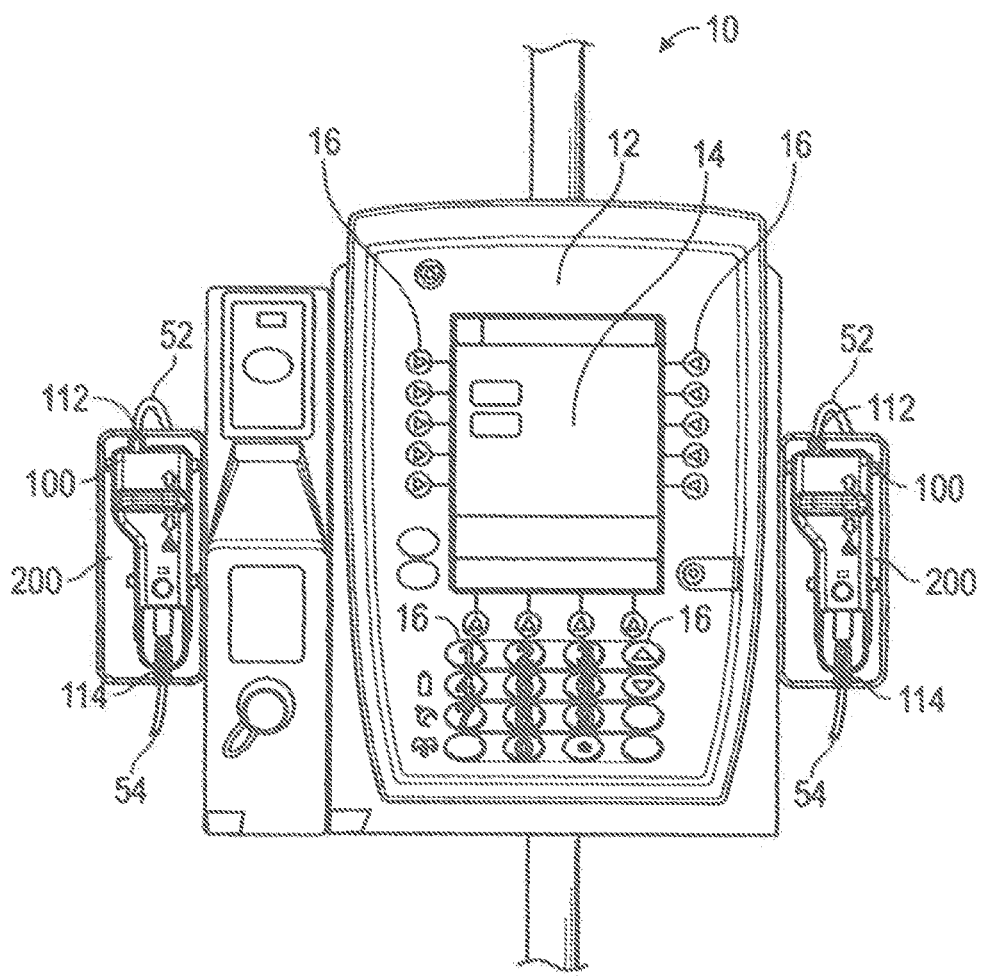
FIGS. 1A and 1B are overview diagrams illustrating examples of infusion pump systems, in accordance with aspects of the present disclosure.

FIG. 1A illustrates an example of an infusion pump system that can contain an embodiment of the air-in-line fitment. It is to be understood that this is only an exemplary infusion pump system, and the air-in-line fitment can be utilized in any type of infusion pump system. The infusion pump system will be generally explained in reference to FIGS. 1-5. An exemplary infusion pump system 10 may include central processing unit 12 with display screen 14 (e.g., touchscreen display), and a data input features 16, for example, a keypad and a series of configurable buttons adjacent to display screen 14. Other types of input and output devices may be used with central processing unit 12 and infusion pump system 10. In certain aspects, central processing unit 12 is operatively coupled to one or more interface modules, with pump cassette recesses 200, to control and communicate with various operational interfaces thereof.

Figure 1B:
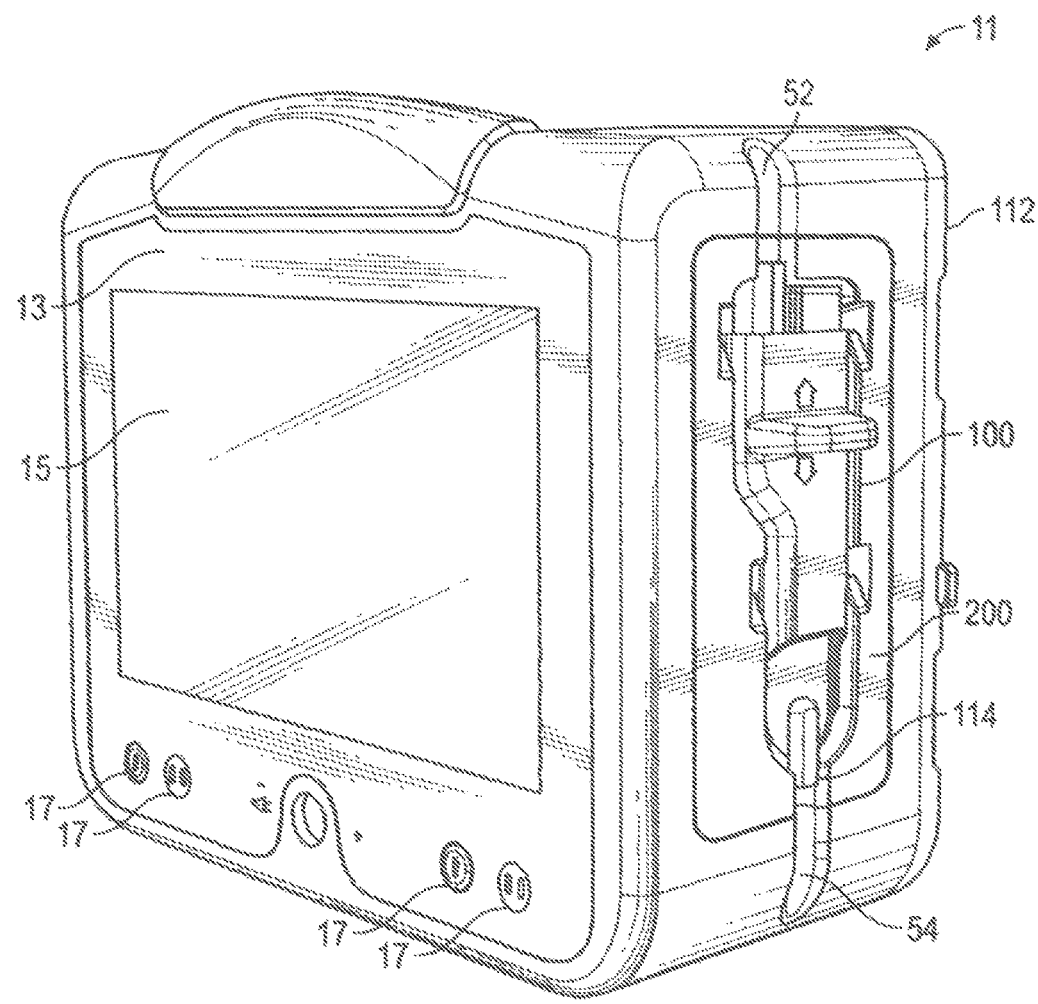

FIG. 1B illustrates another example of an exemplary infusion pump system. This exemplary infusion pump system 11 may include one or more pump cassette recesses 200 and disposable IV pump cassettes 100. For example, pump cassette recess 200 may be configured to receive cassette 100 and provide various mechanical couplings and operational interfaces (e.g., fittings, motor, gearing, driveshaft, sensors, etc.). Infusion pump system 11 may include central processing unit 13 with display screen 15 (e.g., touchscreen display), and data input features 17, for example, a series of configurable buttons adjacent to display screen 15. In some implementations, the display screen 15 may provide a keypad or similar data entry feature. Other types of input and output devices may be used with central processing unit 13 and infusion pump system 11. In certain aspects, central processing unit 13 is operatively coupled to one or more interface modules, with pump cassette recesses 200, to control and communicate with various operational interfaces thereof.

In operation, an IV bag, syringe or other fluid source 52 may be fluidly connected to inlet 112 of cassette 100, and outlet 114 of cassette 100 may be fluidly connected to a patient 54 as shown in the examples of FIGS. 1A and 1B. Cassettes 100 may comprise a DEHP and Latex-free fluid pathway suitable for various patient populations (e.g., neonate, pediatric, and adult).

In operation, a user (e.g., a caregiver) may obtain a new disposable IV cassette 100 and prime cassette 100 before inserting cassette 100 into pump cassette recess 200. The caregiver may check for any visible air bubbles in the fluid pathway and may press on any accessible fluid reservoirs (e.g., pressure dome chambers) to move fluid through the cassette 100. Cassette 100 can be securely held and inserted into pump cassette recess 200 by a single hand of a caregiver. In this regard, caregiver's other hand can be freed to perform other tasks.

Figures 2A, 2B:
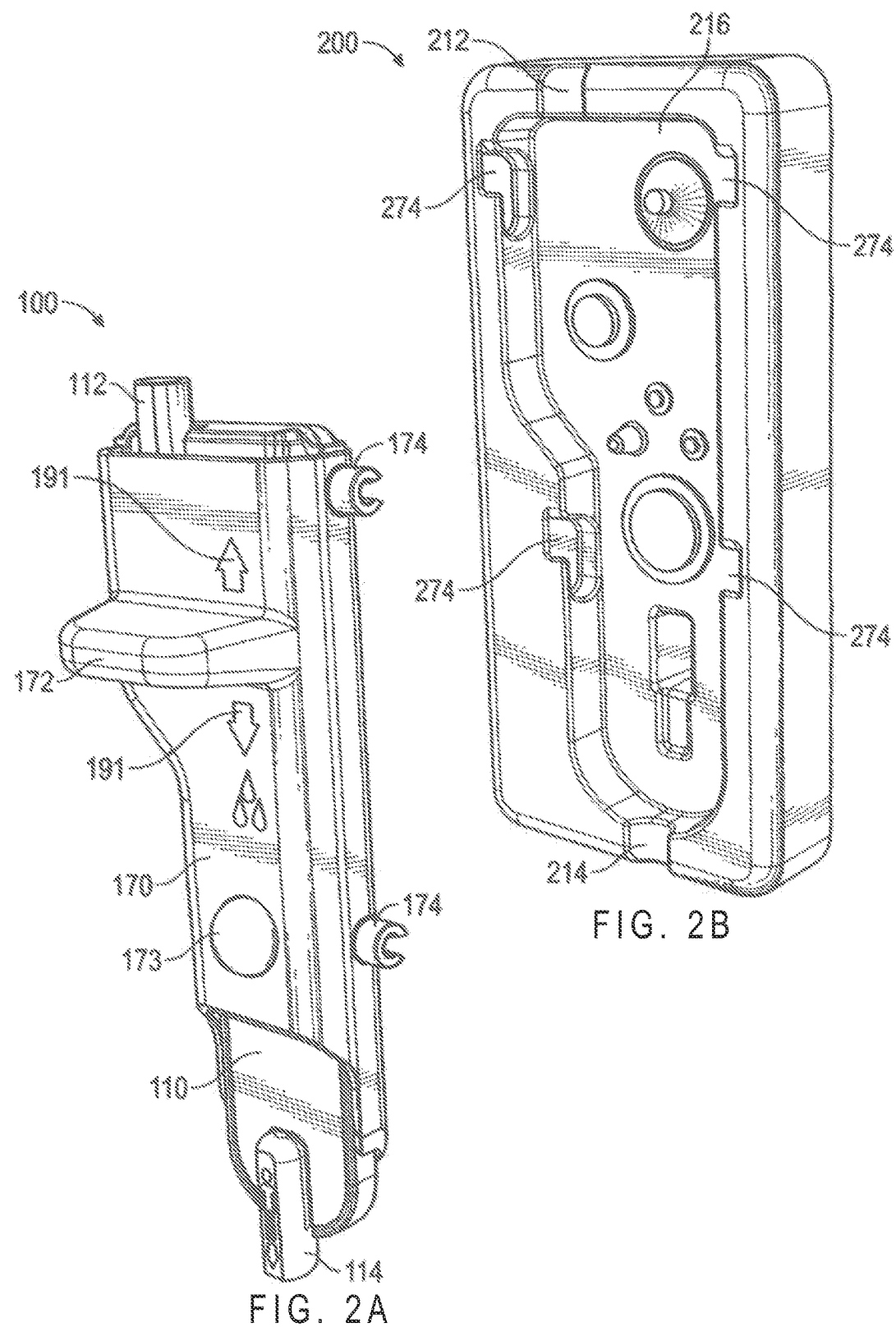
FIGS. 2A and 2B illustrate perspective views of examples of an exemplary embodiment of a disposable IV pump cassette body and pump cassette recess for use with the air-in-line fitment in accordance with aspects of the present disclosure.
Figure 2C:
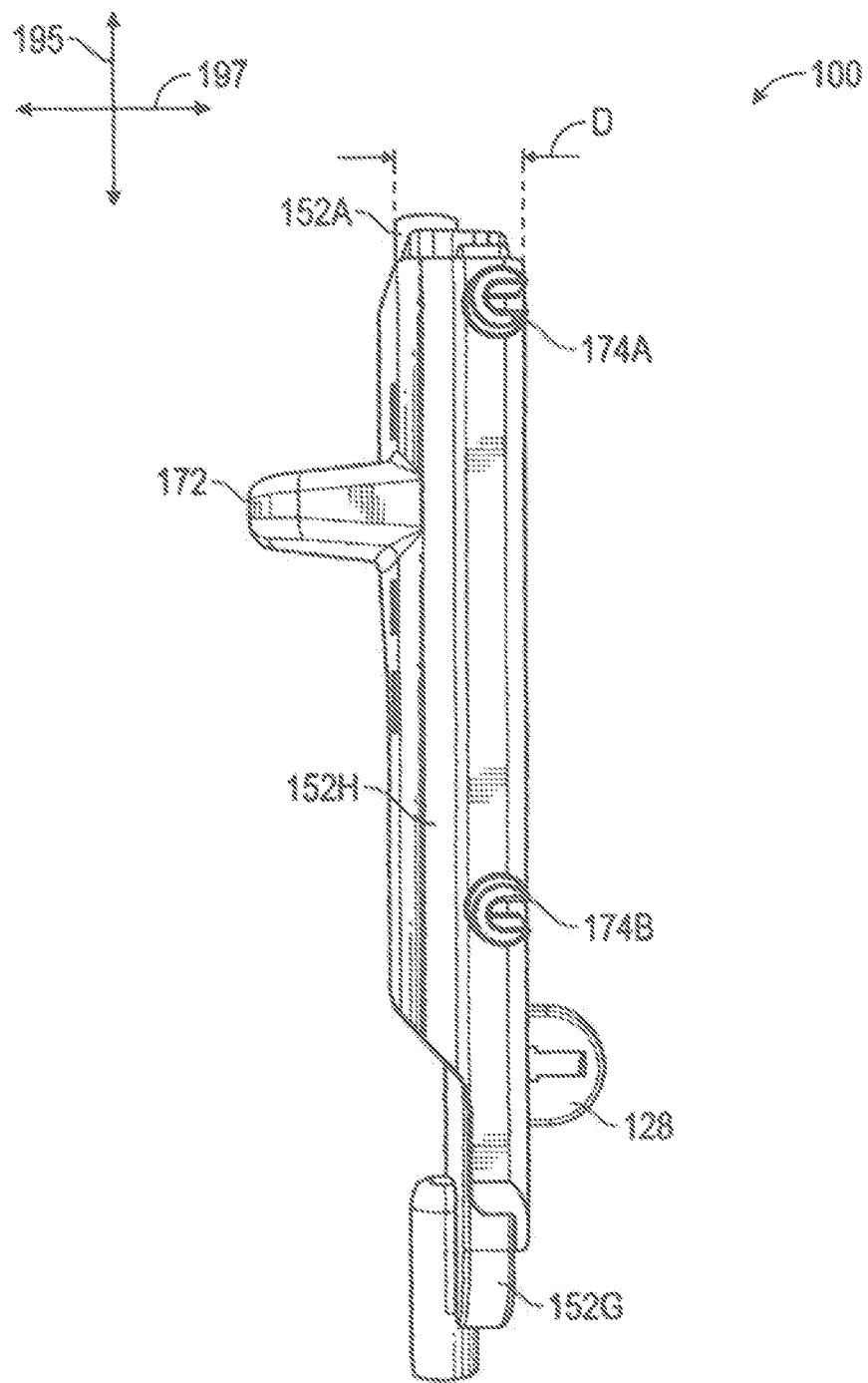
FIG. 2C illustrates a front perspective view of an example of the embodiment of the disposable IV pump cassette body illustrated in FIGS. 2A and 2B, in accordance with aspects of the present disclosure.

FIGS. 2A and 2B illustrate examples of a disposable IV pump cassette 100 and corresponding pump cassette recess 200 of an interface module. Cassette 100 may comprise a pump cassette body 110 and a slider 170. Cassette 100 may include certain may include certain visual indicators related to operation aspects of the cassette and the infusion pump system in general. For example, cassette may include identifiable images such as fluid drops indicating position of slider 170 for free-flow (flow stop valve 164 in an open position) and a patient figure proximal to outlet 114. In accordance with some aspects, cassette 100 may include lens area 173 for magnification of the fluid pathway within the pump cassette body 110. Lens area 173 may be disposed on the slider 170 or proximal to outlet 114 and/or an air-in-line detection feature. For example, during priming or prepping a cassette, a user or caregiver may use lens area 173 to ensure that any visible air bubbles have been removed and fluid is flowing properly. In accordance with some aspects, one or more cassette-seated sensors may be disposed within the pump cassette recess 200 so as to inform central processing unit 12 that the cassette is locked or secured into place within the pump cassette recess 200 or seat.

Slider 170 can be fixably and slidably engaged with pump cassette body 110 such that slider 170 may articulate longitudinally 191 with respect to pump cassette body 110, but will be constrained within range of sliding motion such that the slider remains coupled to the pump cassette body 110. Slider 170 may be formed from rigid plastic or polymer material having lubricating characteristics (e.g., incorporating silicon or polytetrafluoroethylene (PTFE) additives), and is clear or translucent in accordance with certain embodiments. In some embodiments, slider 170 may be polycarbonate. Slider 170 includes a slider grip 172 or handle portion and a plurality of protrusions 174 or lugs that are configured to be releasably lockable with a plurality of slots 274 of the pump cassette recess 200 (e.g., L-shaped locking channels). In this regard, cassette 100 can be self-latched into the pump cassette recess 200. Accordingly, a door or lever action is not required in order to retain the cassette 100 within the pump cassette recess 200. In an alternative embodiment, an inverse configuration may be desired, in which the pump cassette recess 200 would contain protrusions or lugs that would be configured to be releasably lockable with a corresponding slots located on the slider or rigid body.

Depth aspects of cassette 100 is shown in the example of FIG. 2D. Pump cassette body 110, or a substantial portion thereof, may extend depth (D) between 6 mm and 8 mm. Fluid pathway extension member 128 may further extend between 8 mm to 10 mm. In certain aspects, slider grip 172 may extend between 10 mm to 14 mm from pump cassette body 110. It is to be appreciated that the process of cleaning of inlet recess 212, outlet recess 214, and pump cassette recess 200 is made efficient in the shallow recess configuration in accordance with certain embodiments should any fluid or debris accumulate within pump cassette recess 200.

The shallow recess configuration of pump cassette recess 200, and associated longitudinal alignment of cassette 100 such that a smaller of volumetric dimensions of cassette 100 (e.g., depth being smaller than length and width in certain embodiments) further enables additional space for arrangement of mechanical couplings and operational interfaces and optimizes the overall space requirements of pump cassette recess 200 and infusion pump system in general.

In operation, cassette 100 can be loaded directly into pump cassette recess 200. In this regard, the direct loading of the cassette 100 will enable avoidance of sheer forces that might otherwise be applied to the sensors, alignment features, and other engaging interfaces of cassette-facing surface 216 of pump cassette recess 200 from interaction with the interface-facing side of pump cassette body 110 as it is loaded into pump cassette recess 200.

Figure 3:
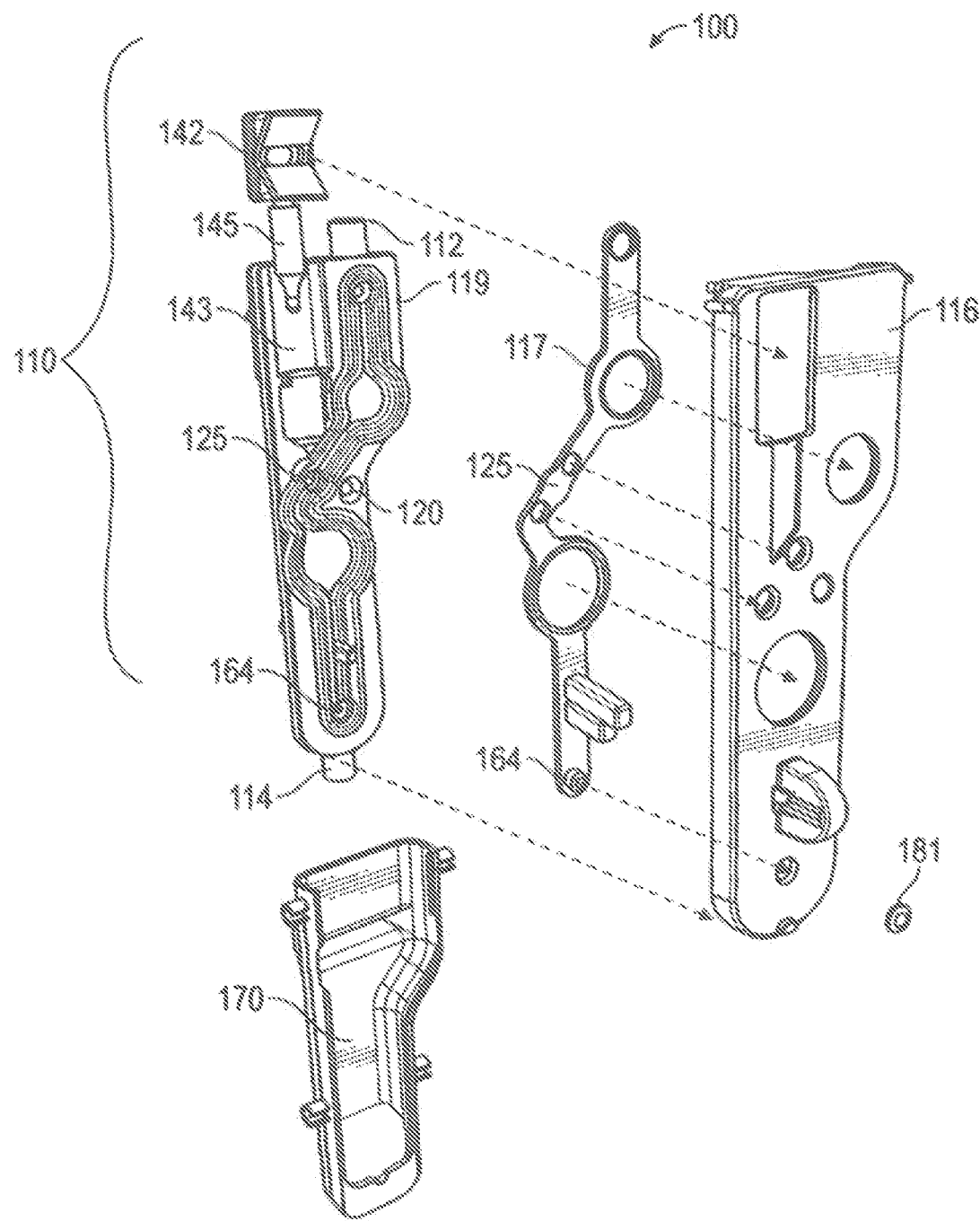
FIG. 3 is an exploded perspective detail view illustrating an example of a first embodiment disposable IV pump cassette body including an embodiment of the air-in-line sensor, in accordance with aspects of the present disclosure.
Figure 4:
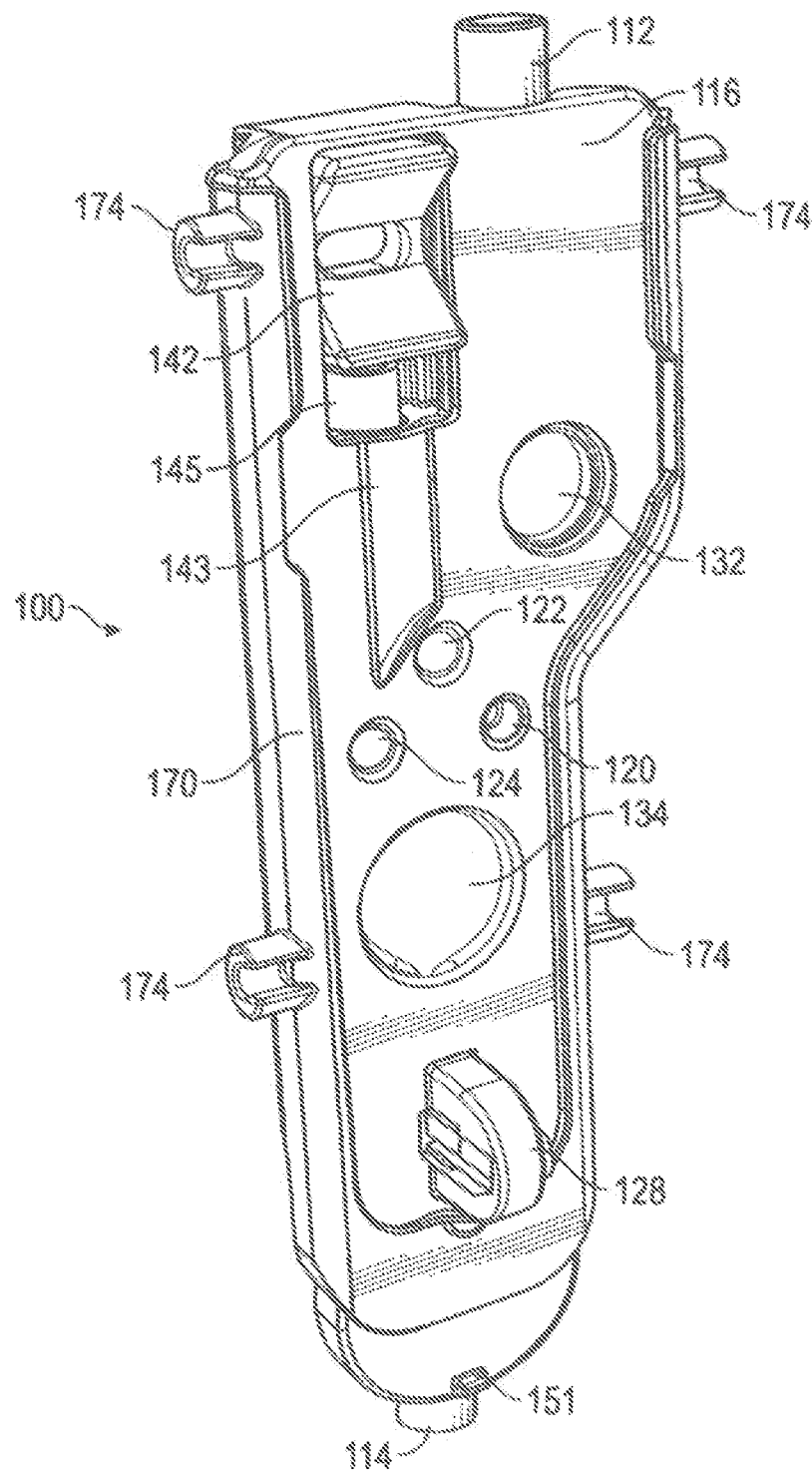
FIG. 4 illustrates a perspective view of an example of a the embodiment of the disposable IV pump cassette body illustrated in FIG. 1, in accordance with aspects of the present disclosure.

Referring now to the examples of FIGS. 3 and 4, pump cassette body 110 may comprise interface-facing frame portion 116 and slider-facing base portion 119 with membrane 117 disposed substantially therebetween (e.g., portions of membrane 117 may extend through some openings of frame portion 116). In accordance with certain embodiments, membrane 117 can be a compliant material co-molded to the frame portion 116 and sealingly engaged with base portion 119 for defining a fluid pathway through pump cassette body 110 from inlet 112 to outlet 114. Mating edges of frame portion 116 and base portion 119 may be connected by fusing, welding, gluing, or the like. Membrane 117 and base portion 119 may further define a plurality of other features, some of which may be accessed through openings in frame portion 116.

Frame portion 116, membrane 117, and/or base portion 119 may define features in or along the fluid pathway, in accordance with certain embodiments. For example, beginning from inlet 112, the fluid pathway may include features such as, but not limited to, upstream pressure dome 132 (e.g., an inlet-side compliant reservoir), inlet-side valve 122, pump chamber having pump chamber opening/access 125, outlet-side valve 124, downstream pressure dome 134 (e.g., an outlet-side compliant reservoir), fluid pathway extension member 128, and flow stop valve 164. Other features that are not in or along the fluid pathway, but are disposed on pump cassette body 110, may include positioning port 120 and slider stopper 151. With respect to extension member 128, a portion of the fluid pathway can be extended away or protrude orthogonally from the generally flat and planar exterior surface of interface-facing frame portion 116 so as to make the fluid in the fluid pathway available for certain detection techniques performed by infusion pump system 10, 11 as further explained below. As illustrated in the example of FIGS. 3 and 4, fluid pathway extension member 128 may be formed from orthogonally extending portions of frame portion 116, membrane 117, and/or base portion 119.

In accordance with certain embodiments, membrane 117 may be formed from a thermoplastic elastomer (TPE). Characteristics of certain TPEs can enable effective co-molding with other materials such as polycarbonate. Accordingly, in some embodiments, membrane 117 may be co-molded to frame portion 116 and striker 181 may be co-molded to a portion of membrane 117 defining a flow stop valve 164. However, in some embodiments, membrane 117 can be formed from silicon, a silicon-based compound, an elastomeric material suitably compliant for fluid flow, or the like.

In accordance with certain embodiments, interface-facing frame portion 116 and slider-facing base portion 119 may be formed from a rigid plastic such as, but not limited, to a polycarbonate. Additionally, the rigid plastic of frame portion 116 and base portion 119 may be clear or translucent. The material of membrane 117 (e.g., TPE or other compliant material) and rigid plastic slider 170 may also be clear or translucent, thereby allowing a user or caregiver to readily observe fluid passage through a substantial portion of the fluid pathway of pump cassette body 110. In some embodiments, the fluid pathway portion of pump cassette body 110 will be clear or translucent, and other portions will be frosted so as to direct a user or caregiver's attention to the fluid pathway.

In some implementations, slider 170, base portion 119, and membrane 117 may be clear or translucent (or at least some portions along the fluid pathway), and the frame portion 116 may not be translucent. For example, the frame portion 116 may be colored in a manner so as to contrast against a color or tint of the fluid expected to be used with cassette 100. In some embodiments, a lens area 173 may be disposed on base portion 119 alternatively, or in addition to, lens area 173 disposed on slider 170.

Figure 5:
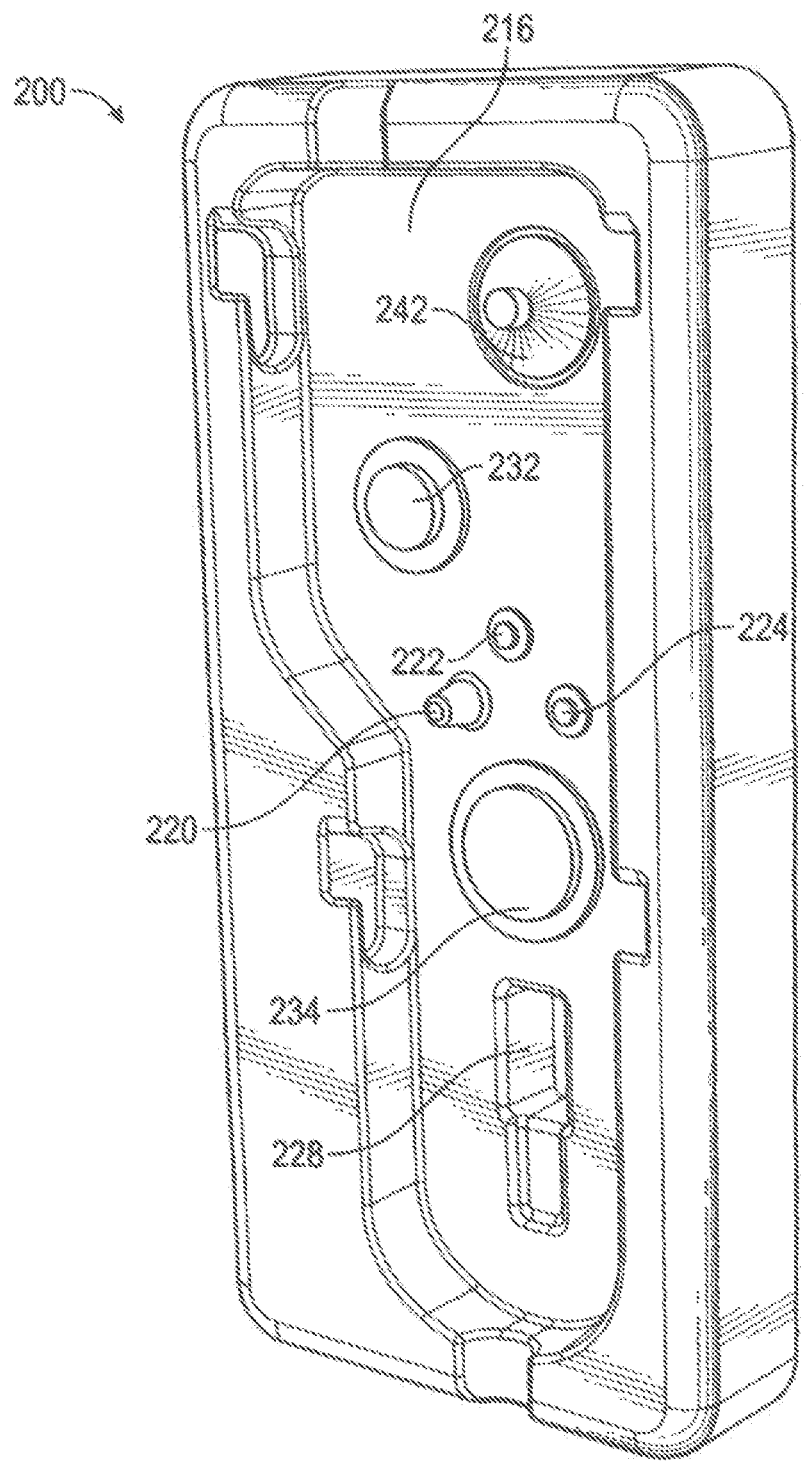
FIG. 5 illustrates a perspective view of an example of a first embodiment of a pump cassette recess, in accordance with aspects of the present disclosure.

With additional reference to the example of FIG. 5, one or more fluid sensors may be disposed within sensor slot 228. The one or more fluid sensors disposed within sensor slot 228 can be ultrasonic sensors configured as an air-in-line detector, for example. In certain embodiments, extension member 128 may be disposed on pump cassette body 110 and positioned along the fluid pathway between downstream pressure dome 134 and flow stop valve 164. However, in some embodiments, extension member 128 can be positioned at other locations along the fluid pathway such as, but not limited to, between inlet 112 and upstream pressure dome 132. Additionally, in other embodiments, a plurality of extension members 128 with a plurality of corresponding sensor slots 228 may be positioned along a fluid pathway of pump cassette body 110.

The positioning of the air-in-line sensor system is illustrated generally as part of multiple embodiments of a pump cassette and infusion pump system in FIGS. 2C, 3, 4 and 5. The purpose of the system is to detect air bubbles in the fluid flow of the IV infusion and to alert a clinician or user via an audio-visual cue or electronic means (such as an alert notice sent to a wireless device) when the volume of air passing through the system reaches or passes a pre-determined threshold. It is also contemplated that the system could automatically stop the flow to the patient if an air bubble is detected, although the preferred method is to alert a clinician or user to the presence of an air bubble in the fluid flow.

The system comprises two parts: a fitment and a sensor. The "fitment" portion of the air-in-line sensor (also referred to as the "fluid pathway extension member") is labeled as 128 while the "sensor slot" portion is labeled as 228. The specifics of the air-in-line sensor will be described in detail with respect to FIGS. 6A-13 using the reference numbers 128 for the fitment and 228 for the sensor slot.

The positioning of the fitment 128 and corresponding sensor slot 228 can vary depending on the design of the pump cassette body 100 and the pump cassette recess 200 into which it is inserted. FIG. 4 shows the fitment 128 positioned on the lower portion of the pump cassette body 100 and FIG. 2B shows the corresponding sensor slot 228 on the lower portion of the pump cassette recess. It should be understood that the positioning of the fitment 128 and corresponding sensor slot 228 can vary depending on the design of the pump cassette body 100 and pump cassette recess 200 and the illustrated embodiments should not be construed to limit the claims.

Figure 6A:
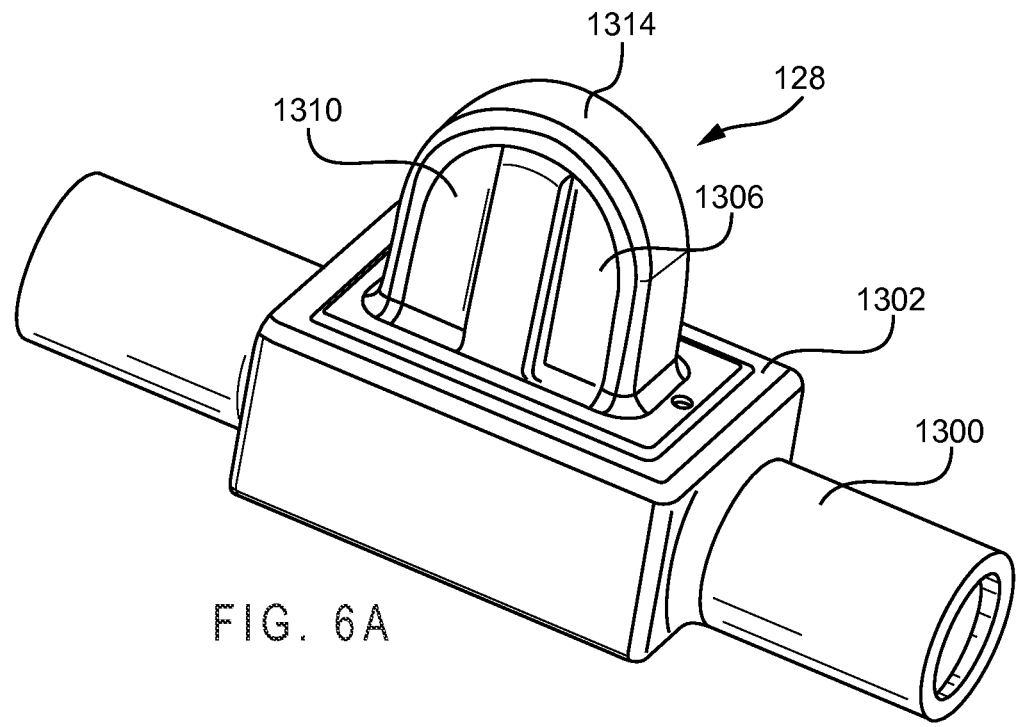
FIG. 6A illustrates a perspective view of an embodiment of an air-in-line fluid detector, in accordance with aspects of the present disclosure.
Figure 6B:
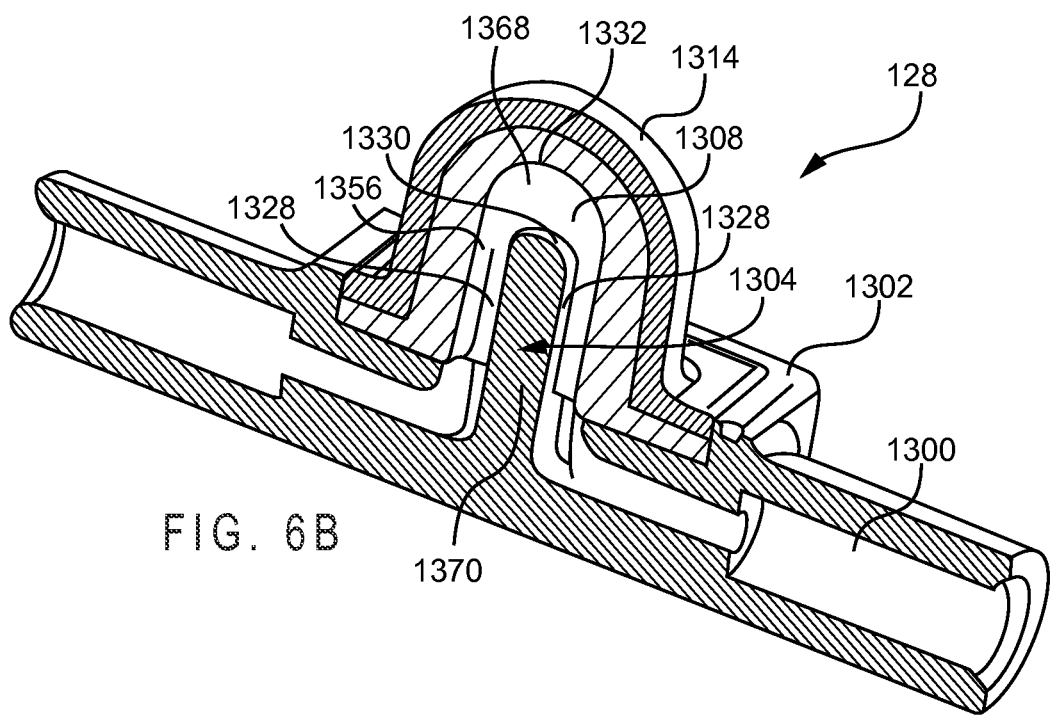
FIG. 6B illustrates a cross-sectional view of the embodiment of FIG. 6A, in accordance with aspects of the present disclosure.
Figure 7:
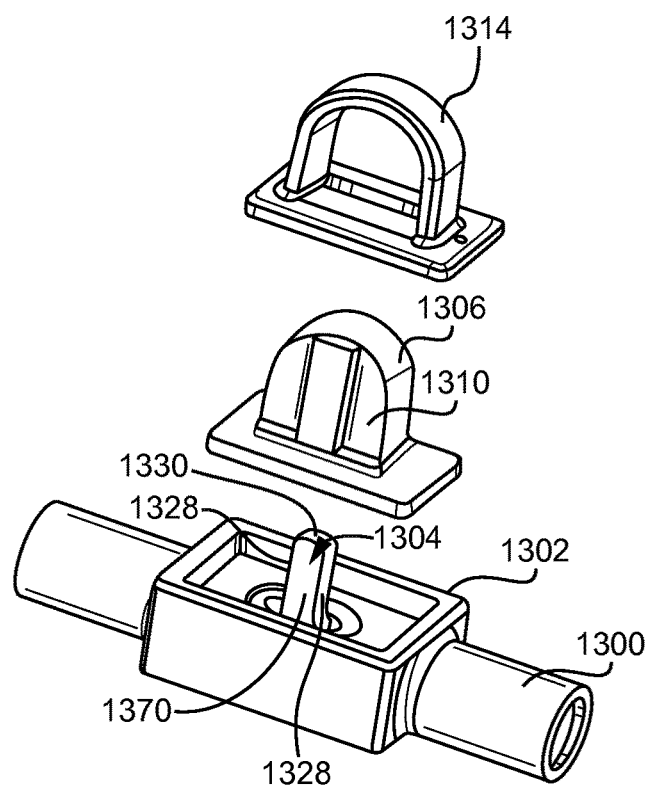
FIG. 7 illustrates an exploded view of the embodiment of FIG. 6A, in accordance with aspects of the present disclosure.
Figure 12:
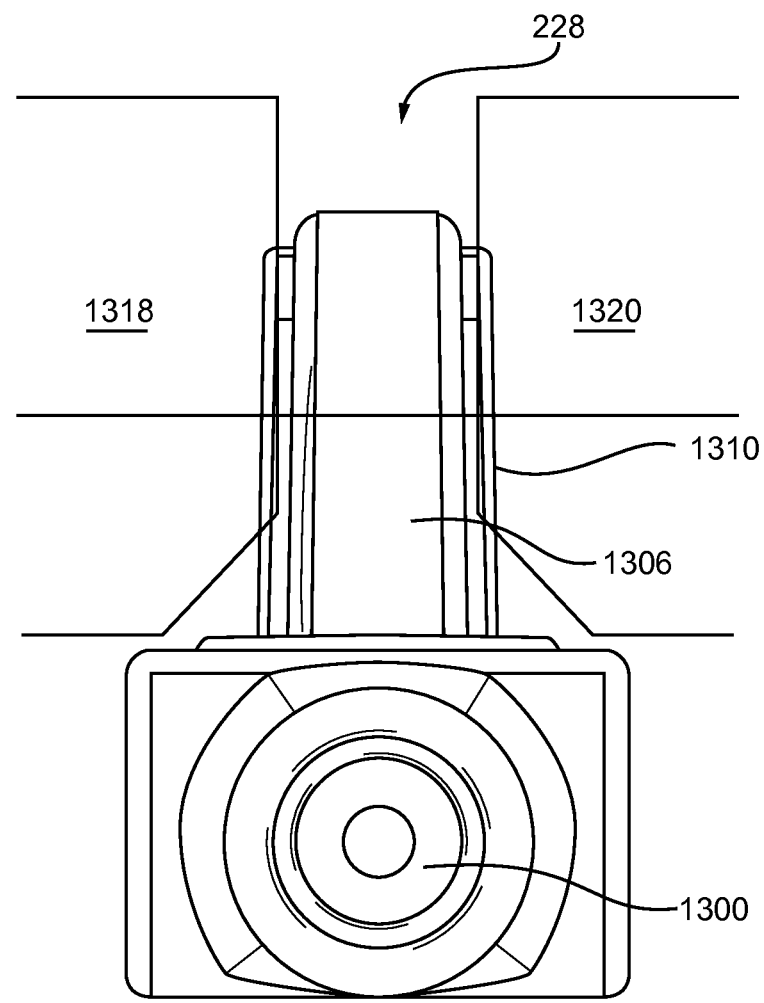
FIG. 12 illustrates a side view of the fitment of FIG. 11 within the slot, in accordance with aspects of the present disclosure.
Figure 13:
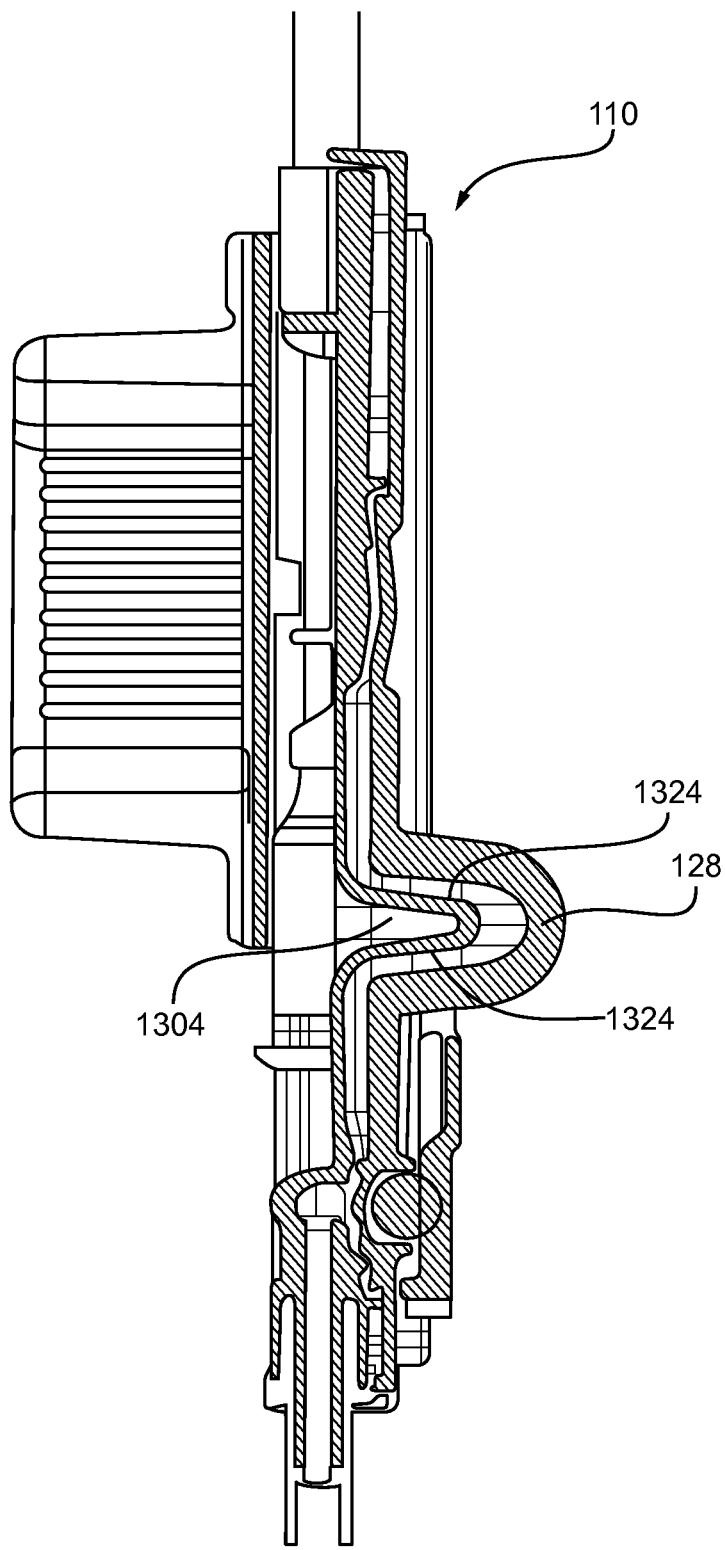
FIG. 13 illustrates a cross-sectional view of an embodiment of a disposable IV pump cassette showing the fluid flow path through the fitment, in accordance with aspects of the present disclosure.

FIGS. 6A, 9B, 11 and 12 illustrate the fitment 128 positioned on a generic IV line 1300, but in operation, the fitment 128 is formed as an integral part of the pump cassette body 100 as shown in FIGS. 4 and 13 for example. Referring to FIGS. 6A and 6B, the fitment 128 includes a base portion 1302 integrally molded into the hard plastic housing 1314 that extends upwards from the pump cassette body 100. The base portion 1302 also includes a flow director vane 1304 integrally molded into the housing of the pump cassette body 100 and extending upwardly from the base portion 1302. The flow director vane 1304 may be hollow, as illustrated in FIG. 10, or solid, as illustrated in FIG. 9. The fitment 128 also includes an elastomeric member 1306 with soft sides and a hollow interior creating a fluid flow path 1308 in conjunction with the flow director vane 1304 as shown in FIG. 6B. The elastomeric member 1306 also includes tapered outside walls 1310. FIG. 17 illustrates an exploded view of the fitment 128.

Referring to FIGS. 10, 10A, 10B and 10C, a specific embodiment of the internal structure of the air-in-line fitment is illustrated. The shape of the flow director vane 1304 in conjunction with the interior shape of the elastomeric member 1306 creates a fluid flow path 1308 that is optimized to improve fluid flow through the sensing area 1322, which is the area between the top 1330 of the flow director vane 1304 and the curved inside wall 1332 of the elastomeric member 1306. The positioning and shape of the flow director vane 1304 is important because the intrusion of the hard plastic of the flow director vane 1304 into the path of the sensing area 1322 can short circuit the acoustic beam used in the sensor.

Figure 9A:
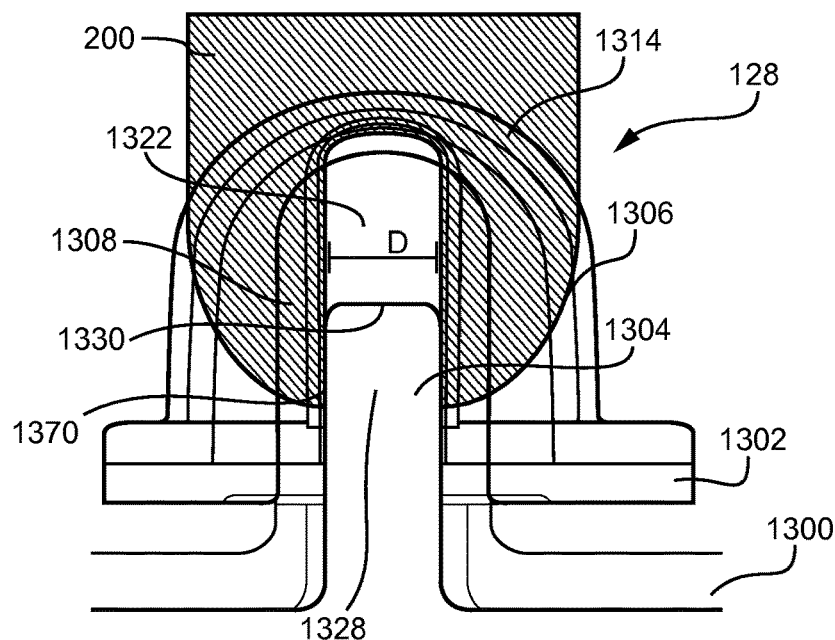
FIG. 9A illustrates a cross-sectional view of the embodiment of FIG. 6A, in accordance with aspects of the present disclosure.
Figure 10:
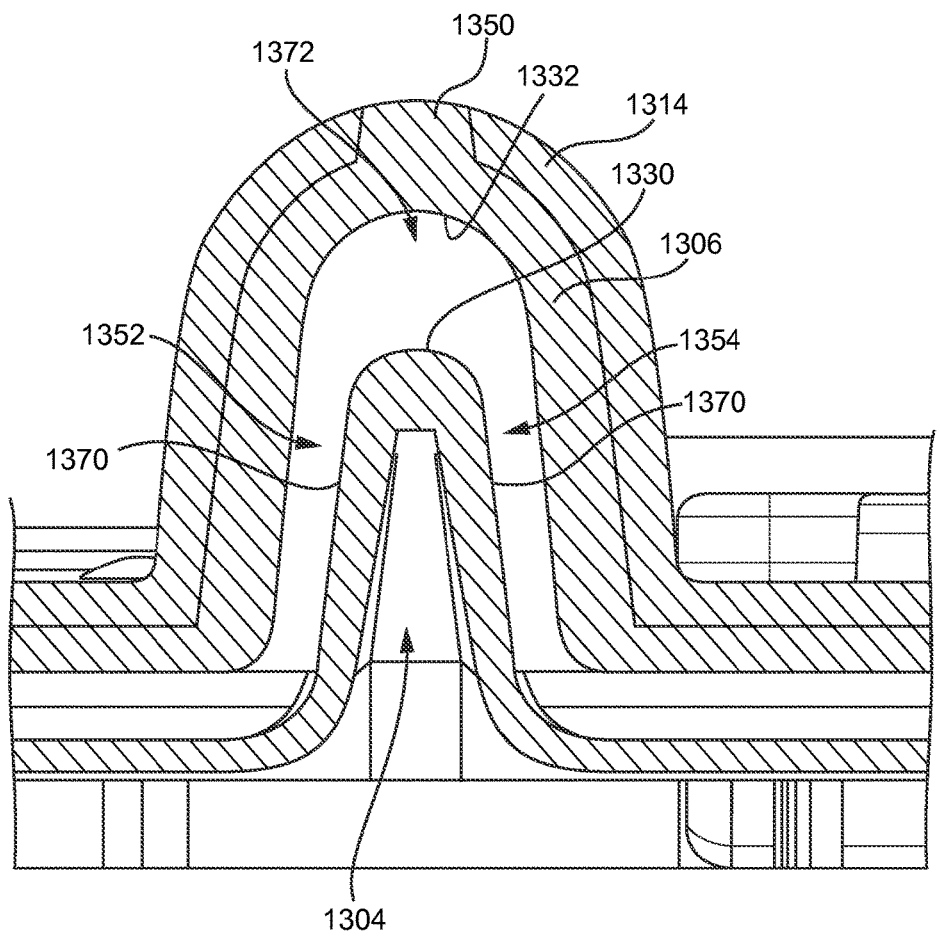
FIG. 10 illustrates an isometric view of an embodiment of an air-in-line fitment in accordance with aspects of the present disclosure.
Figure 11:
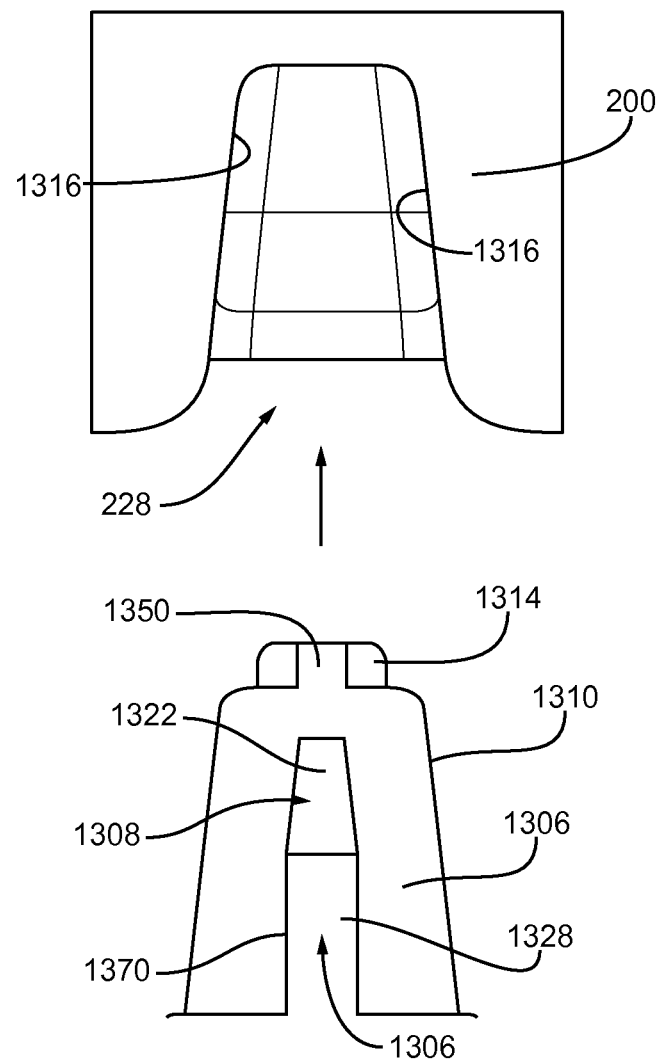
FIG. 11 illustrates a side view of an embodiment of an air-in-line fitment being inserted into a slot, in accordance with aspects of the present disclosure.

The sensing area 1322 is illustrated in cross-section in FIG. 9A. The flow director vane 1304 extends into the elastomeric member 1306 such that the angled flow regions 1324 on the sides 1328 of the flow director vane 1304 are thinner than the portion of the fluid flow path 1308 within the sensing area 1322 above the top 1330 of the flow director vane 1304. This wider portion of the fluid flow path 1308 is a result of the interior of the elastomeric member 1306 having straight internal walls 1334 that extend in a straight line above the top 1330 of the flow director vane 1304 before the curvature 1332 of the elastomeric member 1306 begins.

Furthermore, the curvature of the top 1330 of the flow director vane 1304 substantially matches the inside curvature 1332 of the elastomeric member 1306 as shown in FIG. 10. Referring to FIGS. 10A, 10B and 10C, dimensions of an exemplary embodiment of the fluid flow path 1308 of the fitment 128 are illustrated. It should be noted that these dimensions are exemplary only, and are not meant to limit the disclosure. In one embodiment, the height H at the highest point of the sensing area 1322 of the fluid flow path 1308 from the top of the flow director vane 1304 to the inside curved wall 1332 of the elastomeric member is between about 0.120"-3.05". The flow director vane 1304 has side walls 1328 angled at approximately 14° between the side walls 1328. This creates a tapered flow path 1308 with upstream 1352 and downstream 1354 portions on either side of the flow director vane 1304. In an exemplary embodiment, as shown in FIG. 10A, the angle of the side walls 1328 of the flow director vane 1304 creates distances between the side walls 1328 of the flow director vane 1304 and the side walls 1356 of the elastomeric member 1306 of between about 0.047"-1.19" in a first section 1358 of the upstream portion 1352, between about 0.047"-1.20" in a second section 1360 of the upstream portion 1352, between about 0.060"-1.52" in a third section 1362 of the upstream portion 1352, between about 0.097"-2.47" in a fourth section 1364 of the upstream portion 1352, and between about 0.115"-2.93" in a fifth section 1366 of the upstream portion 1352. The angle of the side walls 1328 of the flow director vane 1304 creates distances between the side walls 1328 of the flow director vane 1304 and the side walls 1356 of the elastomeric member 1306 of between about 0.115"-2.93" in a first section 1374 of the downstream portion 1354, between about 0.097"-2.47" in a second section 1376 of the downstream portion 1354, between about 0.060"-1.52" in a third section 1378 of the downstream portion 1354, between about 0.047"-1.20" in a fourth section 1380 of the downstream portion 1354, and between about 0.047"-1.19" in a fifth section 1382 of the downstream portion 1354.

FIG. 10C illustrates a cross-sectional view of FIG. 10B along line G-G of FIG. 10A. In this exemplary embodiment, the flow director vane 1304 is between about 0.072"-1.84" wide in cross-section with substantially vertical walls 1370. The front and back walls 1368 of the elastomeric member 1306 in this area are situated at an angle of about 12° between them, resulting in a width of between about 0.047"-1.20" at the thinnest area of the top 1372 of the flow path 1308. FIG. 10B illustrates a three-dimensional perspective view of the specialized flow path of this embodiment of the fitment 128. The tapered flow path 1308 that results from these variances in distances creates a fluid flow path 1308 with its largest volume at the top 1372 of the flow path 1308 that tapers down to a smaller volume as the flow path 1308 moves away from the top 1372 of the flow path 1308 into the upstream 1352 and downstream 1354 portions. This creates a total enclosed volume within the sensing area 1322 of about 0.000876 in$^3$.

Figure 8:
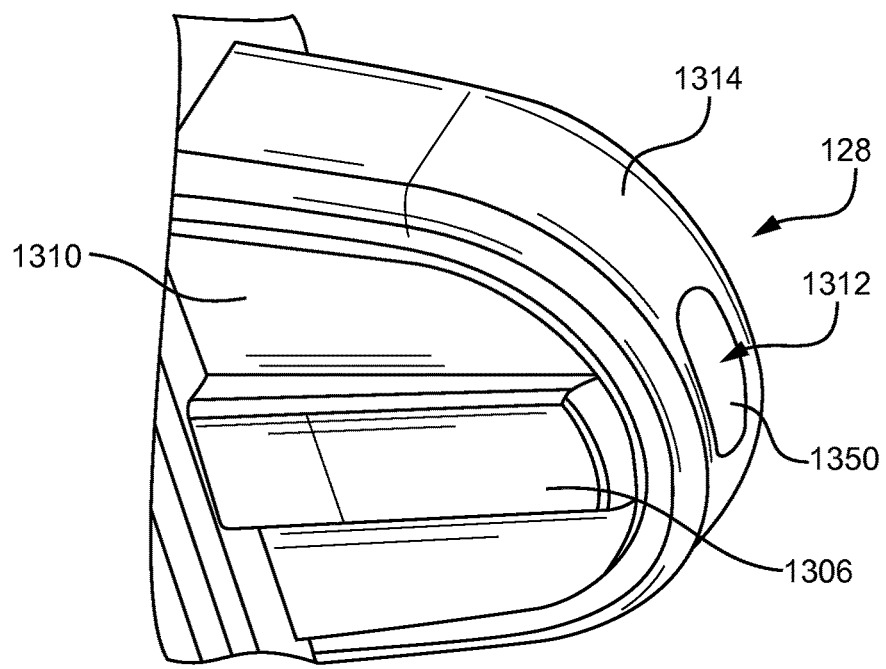
FIG. 8 illustrates a close up perspective view of the embodiment of FIG. 6A, in accordance with aspects of the present disclosure.

The elastomeric member 1306 is co-molded to the hard plastic housing 1314 of the pump cassette body 100 and may include a cored feature 1312 as shown in FIG. 8 to provide secure attachment of the elastomeric member 1306 to the hard plastic housing 1314. The elastomeric member 1306 may include an extension 1350 that fits into the cored feature 1312. The hard plastic housing 1314 is shaped to match the outer curve of the elastomeric member 1306 to ensure that it maintains its interference fit within the hard plastic housing 1314.

The elastomeric member 1306 of the fitment 128 is constructed of a malleable material such as silicone or thermoplastic elastomer (TPE). An exemplary material is an RTV silicone with an approximate shore hardness of 40. Referring to FIG. 10, the use of such material in conjunction with wedge shape formed by the tapered outside walls 1310 allows the fitment 128 to slide into the sensor slot 228 and securely maintain this position due to the interference fit between the inner walls 1316 of the sensor slot 228 and the outer walls 1310 of the fitment 128 as shown in FIG. 12. These tapered outside walls 1310 also maintain a proper acoustic coupling with the sensor as described below. The elastomeric material also resists creep, thus maintaining the proper position of the fluid flow path 1308.

The elastomeric material allows easy insertion of the pump cassette body 100 into the pump cassette recess 200 while ensuring proper positioning. The incorporation of the fitment 128 into the pump cassette body 100 provides automatic insertion of the fitment 128 into the sensor slot 228 due to the alignment features present on the pump cassette body 100 and pump cassette recess 200, thus eliminating mis-loading which can lead to false alarms.

The second portion of the air-in-line sensing system is the sensor. The sensor may be a piezo-electric transducer pair comprising a transmitter 1318 and receiver 1320 positioned on either side of the sensor slot 228 such that when the fitment 128 is inserted into the sensor slot 228, the transmitter 1318 and receiver 1320 are on opposite sides of the fitment 128. Exemplary sensors are an Introtek 8V139 or a PiezoTechnologies 200015 although other sensors known in the art are contemplated.

The sensors are preferably able to detect the air volume within the fluid flow path 1308 with an accuracy within about ±20% for air-in-line alarm limits above 100 µL or within ±20 µL for air-in-line limits equal to or below 100 µL. Additionally, the sensor algorithm is optimized to the fitment 128 to improve its accuracy. When the fitment 128 is in place in the sensor slot 228 and positioned between the sensor's transmitter 1318 and receiver 1320, the fluid flow path 1308 preferably takes up more than 50% of the sensing area 1322 between the transmitter 1318 and receiver 1320.

The specialized horseshoe shape of the fluid flow path 1308 within the fitment 128 has multiple advantages. First, the fluid slows down upon entering the fluid flow path 1308 and speeds up upon exiting the fluid flow path 1308. This convergent-divergent design of the fluid flow path 1308 within the fitment 128 maintains a constant fluid velocity as the fluid travels through the sensing area 1322 of the fitment 128. It also reduces turbulence and results in an absence of large velocity gradients in the sensing area 1322 which improves the monitoring capability of the sensor. Second, the specialized shape of the fluid flow path 1308 provides a thin depth of fluid for scanning while also providing sufficient travel distance for air bubbles through the sensing area 1322.

Third, as illustrated in FIG. 13, when the pump cassette body 100 is loaded into the cassette base 200, the angled fluid flow path 1308 reduces pressure loss and eliminates areas of fluid stagnation that can result in bubbles "sticking" within the fluid flow path 1308. Fourth, the design of the fluid flow path 1308 creates angled flow regions 1324 that reduce the incidence of fluid getting trapped in the fitment 128. This is required as stationary fluid may prevent the system from sensing that the IV container is empty.

Figure 9B:
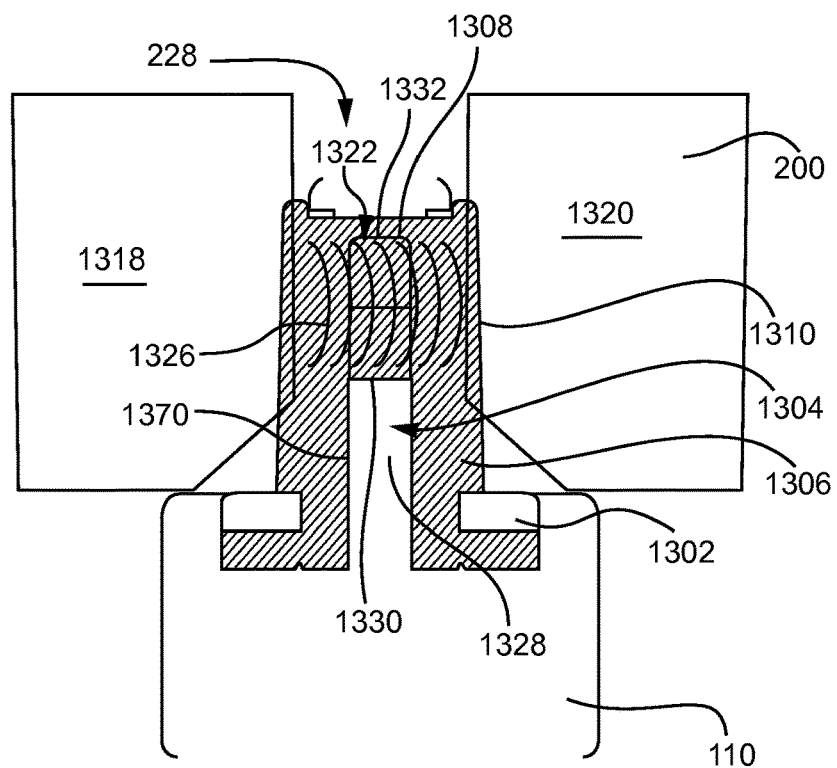
FIG. 9B illustrates a side cross-sectional view of the embodiment of FIG. 6A, in accordance with aspects of the present disclosure.

Referring to FIG. 9B, in operation, ultrasonic energy in the form of an acoustic beam 1326 is generated by the sensor's transmitter 1318 and directed through the sensing area 1322 of the fluid flow path 1308 of the fitment 128 towards the sensor's receiver 1320. Air bubbles flowing through the sensing area 1322 of the fluid flow path 1308 of the fitment 128 pass through the acoustic beam 1326 of the sensor and block the acoustic energy.

Blockage is detected by the sensor's receiver 1320 and electronic components in the sensor monitor this condition and provide an electrical signal. The size of the air bubble can be determined by measuring the time interval of the signal, which indicates the start and end of the air bubble as it passes through the acoustic beam 1326. In operation, if the air bubble exceeds a certain size, the sensor sends a signal to a controller signaling the system to stop the pump operation and to signal the user by way of an audio-visual signal that an air bubble has been sensed within the fluid flow.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A pump cassette body for detecting air bubbles in a fluid pathway, the pump cassette body comprising:
 an upstanding flow director vane;
 a fitment integrally molded into the pump cassette body, the fitment comprising:
  a base integrally molded into the pump cassette body;
  an elastomeric member attached to the base; and
  a housing at least partially surrounding the elastomeric member, wherein the elastomeric member is co-molded to the housing.

Concept 2. The pump cassette body of concept 1 or any other concept, wherein said pump cassette body may removably attach to a pump cassette recess having a slot defined therein, the slot substantially matching the dimensions of the fitment and having opposing walls; and
  an acoustic sensor disposed within the pump cassette recess, the acoustic sensor comprising a transmitter and a receiver, the transmitter and receiver being disposed behind opposite opposing walls of the slot.

Concept 3. The pump cassette body of concept 1 or any other concept, wherein the flow director vane includes angled walls and is disposed within a hollow interior of the elastomeric member to create a substantially U-shaped fluid flow path therein having tapered walls.

Concept 4. The pump cassette body of concept 3 or any other concept, wherein the elastomeric member further comprises tapered outside walls.

Concept 5. The pump cassette body of concept 4 or any other concept, wherein the elastomeric member further comprises tapered inside walls.

Concept 6. The pump cassette body of concept 5 or any other concept, wherein the fluid flow path has a height of between about 0.120" and 3.05" at its highest point.

Concept 7. The pump cassette body of concept 5 or any other concept, wherein the fluid flow path has an upstream portion and a downstream portion, the upstream portion meeting the downstream portion at the highest point of the fluid flow path, the upstream portion having a height of between about 0.047" and 1.19" in a first section of the upstream portion, a height of between about 0.047" and 1.20" in a second section of the upstream portion, a height of between about 0.060" and 1.52" in a third section of the upstream portion, a height of between about 0.097" and 2.47" in a fourth section of the upstream portion, and a height of between about 0.115" and 2.93" in a fifth section of the upstream portion.

Concept 8. The pump cassette body of concept 7 or any other concept, the downstream portion having a height of between about 0.115" and 2.93" in a first section of the downstream portion, a height of between about 0.097" and 2.47" in a second section of the downstream portion, a height of between about 0.060" and 1.52" in a third section of the downstream portion, a height of between about 0.047" and 1.20" in a fourth section of the downstream portion, and a height of between about 0.047" and 1.19" in a fifth section of the downstream portion.

Concept 9. The pump cassette body of concept 1 or any other concept, wherein the elastomeric member is wedge shaped and its widest portion is wider than the sensor slot.

Concept 10. The pump cassette body of concept 1 or any other concept, wherein the housing surrounding the elastomeric member is arcuate.

Concept 11. The pump cassette body of concept 10 or any other concept, wherein the housing surrounding the elastomeric member further comprises an opening and the elastomeric member further comprises an extension that substantially fits in the opening of the housing surrounding the elastomeric member.

Concept 12. The pump cassette body of concept 1 or any other concept, wherein the elastomeric member is a thermoplastic elastomer.

Concept 13. A pump cassette body for detecting air bubbles in a fluid pathway, the pump cassette body comprising:
 a tapered U-shaped fluid flow path defined therein, the tapered fluid flow path having its largest volume at a top portion of the U-shape of the fluid flow path, with the volume tapering down moving away from the top portion of the U-shape of the fluid flow path, the fluid flow path passing through a fluid pathway extension member that is upstanding from the pump cassette body.

Concept 14. The pump cassette body of concept 14 or any other concept, wherein the pump cassette body may removably attach to a pump cassette recess having an opening defined thereon, the opening substantially matching the shape of the fluid pathway extension member, the pump cassette recess having a sensor defined thereon, the sensor having a transmitter and a receiver disposed on opposite sides of the opening.

Concept 15. The pump cassette body of concept 14 or any other concept, wherein the transmitter is capable of transmitting an acoustic beam across the fluid flow path to the receiver to form a sensing area when the pump cassette body is in place in the pump cassette recess.

Concept 16. The pump cassette body concept of claim 15 or any other concept, wherein the extended fluid flow path passes through at least 50% of the sensing area between the transmitter and the receiver when the pump cassette body is in place in the pump cassette recess.

Concept 17. A system for detecting air bubbles in a fluid pathway, the system comprising:
 a pump cassette body having an upstanding flow director vane;
 a fitment integrally molded into the pump cassette body, the fitment comprising:
  a base integrally molded into the pump cassette body;
  an elastomeric member attached to the base;
  a housing at least partially surrounding the elastomeric member, wherein the elastomeric member is co-molded to the housing;
 a pump cassette recess having a slot defined therein, the slot substantially matching the dimensions of the fitment and having opposing walls; and
  an acoustic sensor disposed within the pump cassette recess, the acoustic sensor comprising a transmitter and a receiver, the transmitter and receiver being disposed behind opposite opposing walls of the slot.

Concept 18. The system of concept 17 or any other concept, wherein the fluid flow path has an upstream portion and a downstream portion, the upstream portion meeting the downstream portion at the highest point of the fluid flow path, the upstream portion having a height of between about 0.047" and 1.19" in a first section of the upstream portion, a height of between about 0.047" and 1.20" in a second section of the upstream portion, a height of between about 0.060" and 1.52" in a third section of the upstream portion, a height of between about 0.097" and 2.47" in a fourth section of the upstream portion, and a height of between about 0.115" and 2.93" in a fifth section of the upstream portion.

Concept 19. The system of concept 18 or any other concept, the downstream portion having a height of between about 0.115" and 2.93" in a first section of the downstream portion, a height of between about 0.097" and 2.47" in a second section of the downstream portion, a height of between about 0.060" and 1.52" in a third section of the downstream portion, a height of between about 0.047" and 1.20" in a fourth section of the downstream portion, and a height of between about 0.047" and 1.19" in a fifth section of the downstream portion.

Concept 20. A system for detecting air bubbles in a fluid pathway, the system comprising:
 a pump cassette body having an upstanding flow director vane;
 a fitment integrally molded into the pump cassette body, the fitment comprising:
  a base integrally molded into the pump cassette body;
  an elastomeric member attached to the base;
  a housing at least partially surrounding the elastomeric member;
 a pump cassette recess having a slot defined therein, the slot substantially matching the dimensions of the fitment and having opposing walls such that insertion of the fitment into the slot creates a compression load between the fitment and the walls of the slot; and
  an acoustic sensor disposed within the pump cassette recess, the acoustic sensor comprising a transmitter and a receiver, the transmitter and receiver being disposed behind opposite opposing walls of the slot.

Concept 21. The system of concept 20 or any other concept, wherein the elastomeric member further comprises an extension and the housing further comprises a slot substantially matching the extension.

Concept 22. The system of concept 21 or any other concept, wherein the elastomeric member is comprised of thermoplastic elastomer.

Concept 23. A method of detecting air bubbles in a fluid pathway, the method comprising the steps of:
 providing a pump cassette having an upstanding fitment that includes a tapered fluid flow path therein, the tapered fluid flow path being formed between an upstanding flow director vane and an elastomeric member, the elastomeric member being co-molded to a housing;
 providing a pump cassette recess having an opening that substantially matches the upstanding fitment and includes a sensor having a transmitter and a receiver disposed on opposite sides of the opening;
 inserting the pump cassette into the pump cassette recess such that the fitment is inside the opening;
 sending an acoustic signal from the transmitter to the receiver across the fluid flow path;
 pumping a fluid through the fluid flow path; and
 detecting whether the acoustic signal is received by the receiver.

Concept 24. The method of concept 33 or any other concept, further comprising the step of sending a signal to alarm a user if the acoustic signal is interrupted.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A pump cassette body for detecting air bubbles in a fluid pathway, the pump cassette body comprising:
   a flow director vane; and
   a fitment integrally molded into the pump cassette body, the fitment comprising:
     a base integrally molded into the pump cassette body;
     an elastomeric member attached to the base; and
     a housing surrounding, at least partially, the elastomeric member, wherein the elastomeric member is co-molded to the housing, and wherein the flow director vane and the elastomeric member form a tapered conduit configured to provide, during fluid flow through the pump cassette body, a divergent cross-section of a fluid flow path along a fluid flow direction before a sensing area at a tip of the flow director vane, and a convergent cross-section of the fluid flow path along the fluid flow direction after the sensing area.

2. The pump cassette body of claim 1, wherein said pump cassette body may removably attach to a pump cassette recess having a slot defined therein, the slot substantially matching a dimension of the fitment and having opposing walls; and
   an acoustic sensor disposed within the pump cassette recess, the acoustic sensor comprising a transmitter and a receiver, the transmitter and receiver being disposed behind opposite opposing walls of the slot.

3. The pump cassette body of claim 1, wherein the flow director vane includes angled walls and is disposed within a hollow interior of the elastomeric member to create a fluid flow path therein, the fluid flow path formed in a U-shape and having tapered walls.

4. The pump cassette body of claim 3, wherein the elastomeric member further comprises tapered outside walls.

5. The pump cassette body of claim 4, wherein the elastomeric member further comprises tapered inside walls.

6. The pump cassette body of claim 5, wherein the fluid flow path has a height of between about 0.120" and 3.05" at its highest point.

7. The pump cassette body of claim 5, wherein the fluid flow path has an upstream portion and a downstream portion, the upstream portion meeting the downstream portion at a highest point of the fluid flow path, the upstream portion having a height of between about 0.047" and 1.19" in a first section of the upstream portion, a height of between about 0.047" and 1.20" in a second section of the upstream portion, a height of between about 0.060" and 1.52" in a third section of the upstream portion, a height of between about 0.097" and 2.47" in a fourth section of the upstream portion, and a height of between about 0.115" and 2.93" in a fifth section of the upstream portion.

8. The pump cassette body of claim 7, the downstream portion having a height of between about 0.115" and 2.93" in a first section of the downstream portion, a height of between about 0.097" and 2.47" in a second section of the downstream portion, a height of between about 0.060" and 1.52" in a third section of the downstream portion, a height of between about 0.047" and 1.20" in a fourth section of the downstream portion, and a height of between about 0.047" and 1.19" in a fifth section of the downstream portion.

9. The pump cassette body of claim 1, wherein the elastomeric member is wedge shaped and its widest portion is wider than a sensor slot.

10. The pump cassette body of claim 1, wherein the housing is arcuate.

11. The pump cassette body of claim 10, wherein the housing further comprises an opening and the elastomeric member further comprises an extension that substantially fits in the opening of the housing surrounding the elastomeric member.

12. The pump cassette body of claim 1, wherein the elastomeric member is a thermoplastic elastomer.

13. A system for detecting air bubbles in a fluid pathway, the system comprising:
  a pump cassette body having an upstanding flow director vane;
  a fitment integrally molded into the pump cassette body, the fitment comprising:
    a base integrally molded into the pump cassette body;
    an elastomeric member attached to the base; and
    a housing surrounding, at least partially, the elastomeric member, wherein the elastomeric member is co-molded to the housing, and wherein the elastomeric member forms a wall for a tapered conduit configured to provide, during fluid flow through the pump cassette body, a divergent cross-section of a fluid flow path along a fluid flow direction before a sensing area adjacent to a bend of the elastomeric member, and a convergent cross-section of the fluid flow path along the fluid flow direction after the sensing area;
  a pump cassette recess having a slot defined therein, the slot substantially matching a dimension of the fitment and having opposing walls; and
  an acoustic sensor disposed within the pump cassette recess, the acoustic sensor comprising a transmitter and a receiver, the transmitter and receiver being disposed behind opposite opposing walls of the slot.

14. The system of claim 13, wherein a fluid flow path has an upstream portion and a downstream portion, the upstream portion meeting the downstream portion at a highest point of the fluid flow path, the upstream portion having a height of between about 0.047" and 1.19" in a first section of the upstream portion, a height of between about 0.047" and 1.20" in a second section of the upstream portion, a height of between about 0.060" and 1.52" in a third section of the upstream portion, a height of between about 0.097" and 2.47" in a fourth section of the upstream portion, and a height of between about 0.115" and 2.93" in a fifth section of the upstream portion.

15. The system of claim 14, the downstream portion having a height of between about 0.115" and 2.93" in a first section of the downstream portion, a height of between about 0.097" and 2.47" in a second section of the downstream portion, a height of between about 0.060" and 1.52" in a third section of the downstream portion, a height of between about 0.047" and 1.20" in a fourth section of the downstream portion, and a height of between about 0.047" and 1.19" in a fifth section of the downstream portion.

16. A system for detecting air bubbles in a fluid pathway, the system comprising:
  a pump cassette body having a flow director vane;
  a fitment integrally molded into the pump cassette body, the fitment comprising:
    a base integrally molded into the pump cassette body;
    an elastomeric member attached to the base; and
    a housing surrounding, at least partially, the elastomeric member, wherein the flow director vane and the elastomeric member form a tapered conduit configured to provide, during fluid flow through the pump cassette body, a divergent cross-section of a fluid flow path along a fluid flow direction before a sensing area at a tip of the flow director vane, and a convergent cross-section of the fluid flow path along the fluid flow direction after the sensing area;
  a pump cassette recess having a slot defined therein, the slot substantially matching the fitment and having opposing walls such that insertion of the fitment into the slot creates a compression load between the fitment and a wall of the slot; and
  an acoustic sensor disposed within the pump cassette recess, the acoustic sensor comprising a transmitter and a receiver, the transmitter and receiver being disposed behind opposite opposing walls of the slot.

17. The system of claim 16, wherein the elastomeric member further comprises an extension and the housing further comprises a slot substantially matching the extension.

18. The system of claim 17, wherein the elastomeric member is comprised of thermoplastic elastomer.

* * * * *